United States Patent
Snow

(10) Patent No.: US 10,695,017 B2
(45) Date of Patent: Jun. 30, 2020

(54) SMALL ANIMAL X-RAY POSITIONER

(71) Applicant: KONICA MINOLTA HEALTHCARE AMERICAS, INC., Wayne, NJ (US)

(72) Inventor: Terry Snow, Oak Harbor, WA (US)

(73) Assignee: KONICA MINOLTA HEALTHCARE AMERICAS, INC., Wayne, NJ (US)

( * ) Notice: Subject to any disclaimer, the term of this patent is extended or adjusted under 35 U.S.C. 154(b) by 0 days.

(21) Appl. No.: 16/263,341

(22) Filed: Jan. 31, 2019

(65) Prior Publication Data
US 2019/0239828 A1 Aug. 8, 2019

Related U.S. Application Data

(60) Provisional application No. 62/625,852, filed on Feb. 2, 2018.

(51) Int. Cl.
*A61B 6/00* (2006.01)

(52) U.S. Cl.
CPC ............ *A61B 6/4405* (2013.01); *A61B 6/508* (2013.01)

(58) Field of Classification Search
CPC ........... A61B 6/04; A61B 6/4405; A61B 6/46; A61B 6/587; A61B 6/0407; A61B 6/4283; A61B 6/508
See application file for complete search history.

(56) References Cited

U.S. PATENT DOCUMENTS

| | | | | |
|---|---|---|---|---|
| 4,752,948 | A * | 6/1988 | MacMahon | A61B 6/4405 378/193 |
| 9,125,611 | B2 * | 9/2015 | Eaves | A61B 6/4405 |
| 9,414,795 | B2 * | 8/2016 | Nakata | A61B 6/4429 |
| 2003/0142788 | A1* | 7/2003 | Cho | A61B 6/4405 378/102 |
| 2010/0054422 | A1* | 3/2010 | Ohmura | A61B 6/4405 378/196 |

* cited by examiner

*Primary Examiner* — Chih-Cheng Kao
(74) *Attorney, Agent, or Firm* — Lucas & Mercanti, LLP

(57) ABSTRACT

An x-ray positioning stand, for holding an x-ray generator, includes a base having a primary base member, a first extension arm, and a second extension arm. The primary base member extends in a longitudinal direction along the length from a first end to a second end, and extends in a transverse direction along the width from a front side to a rear side. The first extension arm is pivotably connected to the primary base member proximate the first end and the second extension arm is pivotably connected to the primary base member proximate the second end. The stand also includes a support rod having a lower end connected to a central portion of the primary base member and an upper end having an attachment head connectable to the x-ray generator, and configured for supporting the x-ray generator over a subject to be imaged. Each of the first extension arm and the second extension arm are pivotable from a stored position to a deployed position. The free ends of the first extension arm and the second extension arm are closer to each other in the stored position than in the deployed position.

20 Claims, 13 Drawing Sheets

SMALL ANIMAL X-RAY POSITIONER

CROSS-REFERENCE TO RELATED APPLICATIONS

The present invention claims the priority of U.S. Provisional Patent Application 62/625,852, filed Feb. 2, 2018, the entire contents of which are incorporated herein by reference.

BACKGROUND OF THE INVENTION

The present invention relates to an X-ray positioner that holds an X-ray generator in position above or next to a subject to be irradiated.

When a veterinarian or veterinary technician visits a remote location outside of a veterinary office to take an X-ray of a small animal patient, it can be difficult to position all the pieces of equipment and hold the patient. This is especially the case when the veterinarian or veterinary technician makes the visit alone.

Although X-ray tables exist, which can be wheeled around an office, these tables are cumbersome to transport to locations remote from the veterinary office. As such, they are not a viable option for a traveling veterinarian or veterinary technician.

BRIEF SUMMARY OF THE INVENTION

An object of the present invention is to provide a positioner for holding an x-ray generator that is transportable and can safely hold the x-ray generator above a subject to be irradiated and imaged.

The object is met by an x-ray positioning stand for holding an x-ray generator, including a base having a primary base member, a first extension arm, and a second extension arm. The primary base member extends in a longitudinal direction along the length from a first end to a second end, and extends in a transverse direction along the width from a front side to a rear side. The first extension arm is pivotably connected to the primary base member proximate the first end and the second extension arm is pivotably connected to the primary base member proximate the second end. The stand also includes a support rod having a lower end connected to a central portion of the primary base member and an upper end having an attachment head connectable to the x-ray generator, and configured for supporting the x-ray generator over a subject to be imaged. Each of the first extension arm and the second extension arm are pivotable from a stored position to a deployed position, wherein the primary base member, the first extension arm and the second extension arm provide a support for the x-ray generator when the x-ray generator is connected to the support rod in the deployed position. The free ends of the first extension arm and the second extension arm are closer to each other in the stored position than in the deployed position. In a preferred embodiment, the first extension arm and the second extension arm are parallel to the longitudinal direction of the primary base member in the stored position.

The support rod includes an upper part and a lower part extendable with respect to each other and a locking mechanism that is movable from a locked position in which the upper part and lower part are fixed with respect to each other by the locking mechanism, and a released position in which the upper part and lower part are movable with respect to each other so that a length of the support rod is adjustable.

In a preferred embodiment, the lower part and the upper part of the support rod are telescopically movable with respect to each other.

In one embodiment of the present invention, each of the first extension arm and the second extension arm include telescopically extendable parts. This allows the first extension arm and the second extension arm to be shortened in the stored position and made longer in the deployed position to provide a more stable base for supporting the x-ray generator.

In a further embodiment of the present invention, the support rod is pivotably connected to the base about a pivot axis that is perpendicular to the longitudinal axis of the base plate, and the x-ray positioning stand further comprises a positioning device for selectively maintaining the support rod at a fixed position relative to the base plate. This feature allows the x-ray generator to be held at an oblique angle relative to a radiographic panel on the floor.

To hold the support rod at the fixed position, the positioning device includes a pivot index plate with a plurality of holes spaced circumferentially about the pivot axis and a pin that is engagable in one of the plurality of holes and with the support rod.

In a preferred embodiment, the base further includes a handle facilitating carrying the positioning device to remote locations.

In a preferred embodiment, the handle is connected to the rear side of the base plate. However, the handle can be disposed at any location that is ergonomically advantageous.

In yet a further embodiment, the primary base member is a plate having a upper surface and a lower surface, the support rod being connected at the upper surface. The plate is preferably made of aluminum. However, the plate can be made of any material such as metal, metal alloys, or plastics. In this embodiment, the first extension arm and the second extension arm are connected at the lower surface of the primary base member. The primary base member includes ribs on the lower surface creating pockets that receive the first extension arm and the second extension arm in the stored position of the first extension arm and the second extension arm.

In a specific embodiment, three ribs are disposed at the first end, the second end, and a central location of the primary base member, the three ribs extending in the transverse direction, and a further rib is disposed along the rear side. A bottom surface of the ribs and a bottom surface of the first and second extension arms are preferably disposed in a same plane against the ground when the stand is in use in the deployed position of the first and second extension arms.

In a further embodiment, the attachment head includes two side plates separated by a space, and an x-ray generator adaptor connectable to the x-ray generator, the x-ray generator adaptor being insertable into the attachment head between the side plates to connect the x-ray generator to the attachment head.

In a preferred embodiment, the x-ray generator adapter is a bar having a first end connectable to the x-ray generator and a second end insertable between the side plates, wherein the bar includes two bosses projecting from two opposing sides of the bar between the first end and the second, the bosses being receivable in respective slots in the side plates.

Each of the slots of the side plates has an open end and a closed end, the closed end disposed at a bottom section of the slot. In a preferred embodiment, the slots are vertical slots with open end being the upper end of the slot at the upper end of the side plates. However, the slots could have any other shapes or arrangements such as L-shaped, curved, or angled.

The attachment head further includes a stop arranged between side plates. when the bosses are received at the bottom sections of the slots and the first end of the bar is connected to the x-ray generator, the top of the second end of the bar is held against the stop by a weight of the x-ray generator at the first end.

In yet a further embodiment of the present invention, a spring connected between the base and the support rod urging the support rod to a deployed position. The spring is arranged to automatically raise the support rod from a stored position to the deployed position when the support rod is released from the stored position. The spring is preferably a gas spring comprising a piston-cylinder. However, a coil spring could alternatively be used. In one embodiment, the spring is connected to the support rod by a cable. However, the spring could also be directly connected to the support rod.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 1A is a perspective view of another embodiment of a base of the x-ray positioner stand according to the present invention;

DETAILED DESCRIPTION OF THE PREFERRED EMBODIMENTS

Figure 1:
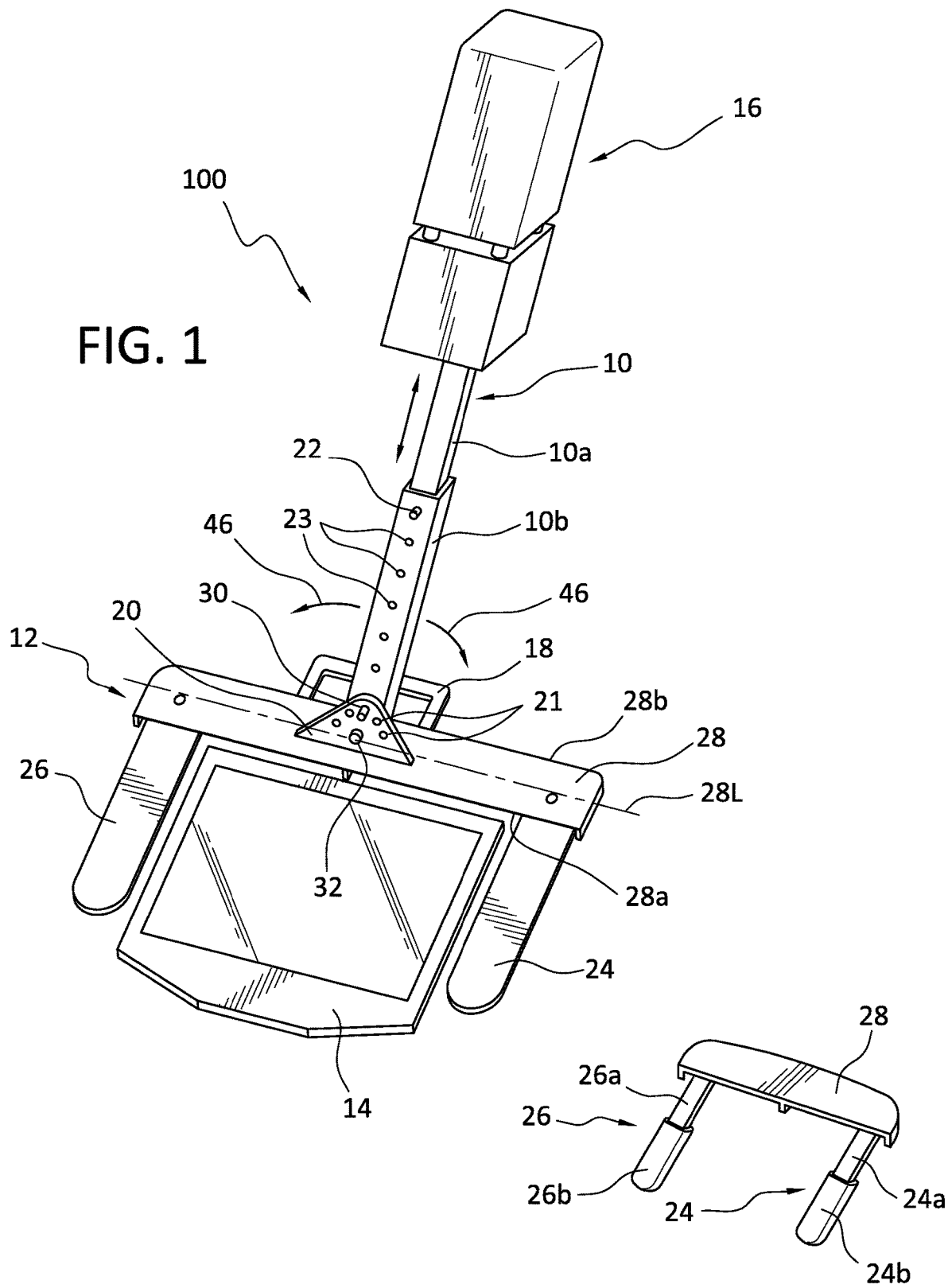
FIG. 1 is a perspective view of an x-ray positioner stand in an open position according to an embodiment of the present invention.

A first embodiment of the small animal x-ray positioner stand 100 according to the present invention shown in FIG. 1 includes a support rod connected to a base 12. The support rod 10 includes an upper part 10*a* and a lower part 10*b*. The upper part 10*a* is inserted into the lower part 10*b* so that the length of the support rod 10 is adjustable telescopically. The lower part 10*b* includes multiple holes along its length so that the upper and lower parts of the support rod 10 can be locked relative to each other at multiple lengths using a spring-loaded pin 22, which is housed in the upper part 10*a*. Instead of a spring-loaded pin, a push pin or cam lock can also be used to lock the upper and lower parts of the support rod 10 relative to each other. An x-ray generator 16 is mounted to the upper part 10*a* of the support rod 10. The lower part 10*b* is mounted on the base 12.

The base 12 includes a base plate 28 and two extension arms 24, 26. The base plate 28 has a length along a longitudinal axis 28L and a width between a front edge 28*a* and a rear edge 28*b*. The extension arms 24, 26 are pivotably connected to the base plate 28. FIG. 1 shows the extension arms 24, 26 in a deployed position in which the extension arms extend from the front edge 28*a* of the base plate 28. FIG. 1 shows the extension arms 24, 26 deployed perpendicular to the longitudinal direction 28L. As an alternative, the extension arms 24, 26 may also be deployed at an oblique or acute angle relative to the longitudinal direction 28L. The base 12 also includes a handle 18 connected at the rear edge 28*b* of the base plate 28. The deployed position of the extension arms 24, 26 provides a stable support with the base plate 28 for holding the x-ray generator 16 above a patient to be imaged. The base plate 28 is approximately 2' to 3' in length along the longitudinal axis 28L so that a distance between extension arms 24, 26 in the deployed position allows for a radiographic panel 14 to be placed between the deployed extension arms 24, 26 to capture an image (see also FIG. 17). The x-ray generator 16 is held approximately 1.5' to 3' above a patient.

The lower part 10*b* of the support rod 10 is pivotally mounted to a pivot index plate 20 mounted on the base plate 28. The pivot index plate 20 includes a plurality of holes 21 spaced circumferentially about a pivot axis 32. The support rod 10 can pivot about the pivot axis 32 (see arrows 46) and the support rod 10 is maintained at a fixed position relative to the base 12 when a spring-loaded pin 30, which is housed in a lower end of the lower part 10*b*, is inserted in one of the holes 21. Instead of a spring-loaded pin, a push pin can alternatively be used. This allows the support rod 10 to be positioned at oblique angles relative to a radiographic panel 14 arranged on the floor below the x-ray generator 16.

FIG. 1A shows an alternative embodiment in which each of the extension arms 24, 26 includes two parts 24a, 24b and 26a, 26b that are movable relative to each other to extend or contract the length of the respective extension arms. The two parts 24a, 24b and 26a, 26b may be telescopically inserted one in the other or they may be connected, e.g., by a slotted guide.

Figure 2:
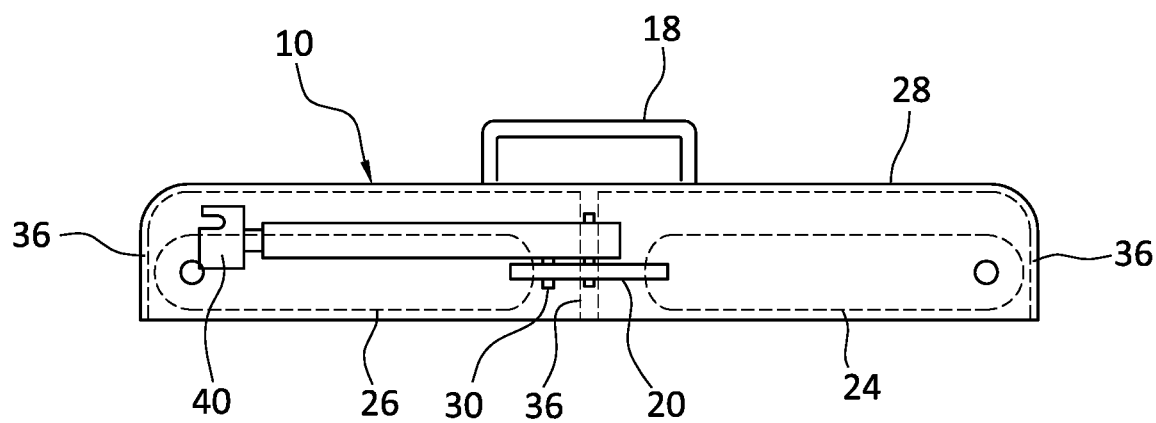
FIG. 2 is a top view of the x-ray positioner stand of FIG. 1 in a transport mode.

FIG. 2 shows the positioner stand 100 arranged in a transport mode in which the extension arms 24, 26 (shown in dashed lines) are pivoted to a transport position under the base plate 28 so that free ends of the extension arms are closer to each other in the transport position than in the deployed position shown in FIG. 1. In the transport mode, the support rod 10 is locked at its shortest length, and the support rod 10 is locked relative to the pivot index plate 20 at a stored position, which is closest to the base plate 28. In a preferred embodiment, the extensions arms 24, 26 extend parallel to the longitudinal axis 28L in the transport position and the support rod 10 is also parallel to the longitudinal axis 28L in the stored position. An attachment head 40 for holding the x-ray generator 16 on the support rod 10 is shown schematically in FIG. 2 and is described in more detail below.

Figure 3:
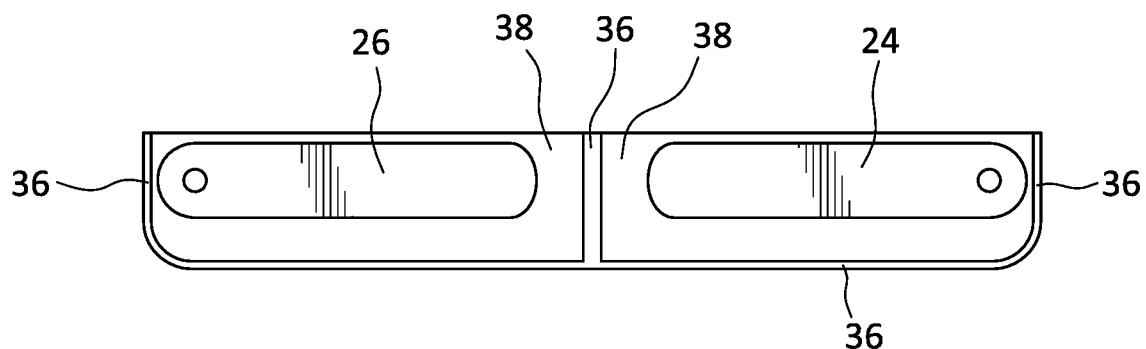
FIG. 3 is a bottom view of the x-ray positioner stand of FIG. 1 in the transport mode.
Figure 4:
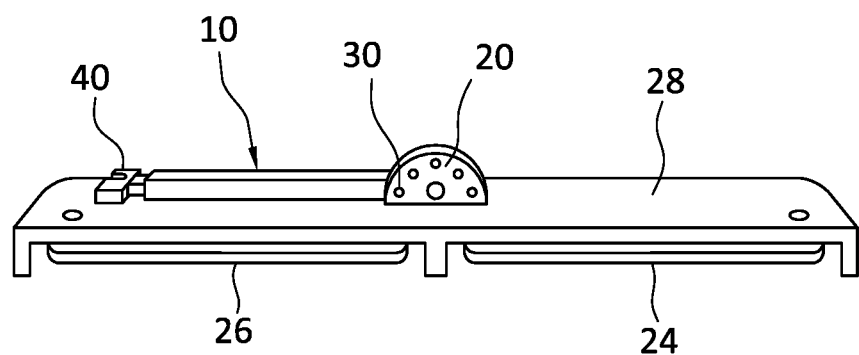
FIG. 4 is a front perspective view of the x-ray positioner stand of FIG. 1 in the transport mode.

FIGS. 3 and 4 shows a bottom side of the base plate 28 and a perspective front and top view of the base plate 28 in the transport mode. The base plate 28 includes ribs 36 that extend downward and form pockets 38, 38 in which the extension arms 24 and 26 are received in the transport position. The ribs 36 also help stabilize the base plate 28 when the stand supports the x-ray generator 18.

Although the extension arms 24, 26 are depicted on the lower surface of the base plate 28, it is also possible to connect the extension arms 24, 26 at a top surface of the base plate 28.

Figure 5:
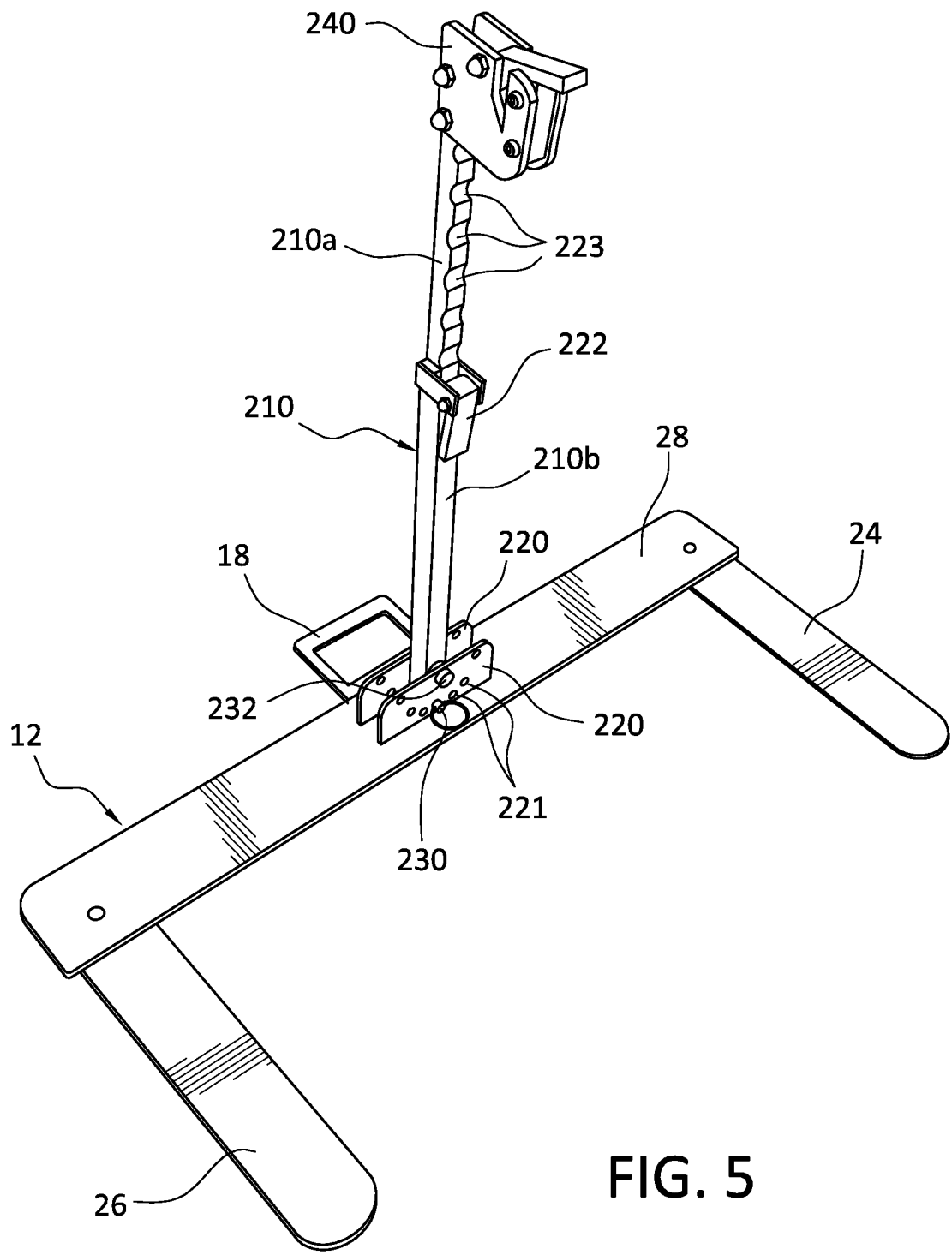
FIG. 5 is a perspective view of an x-ray positioner stand in an open position according to another embodiment of the present invention.
Figure 6:
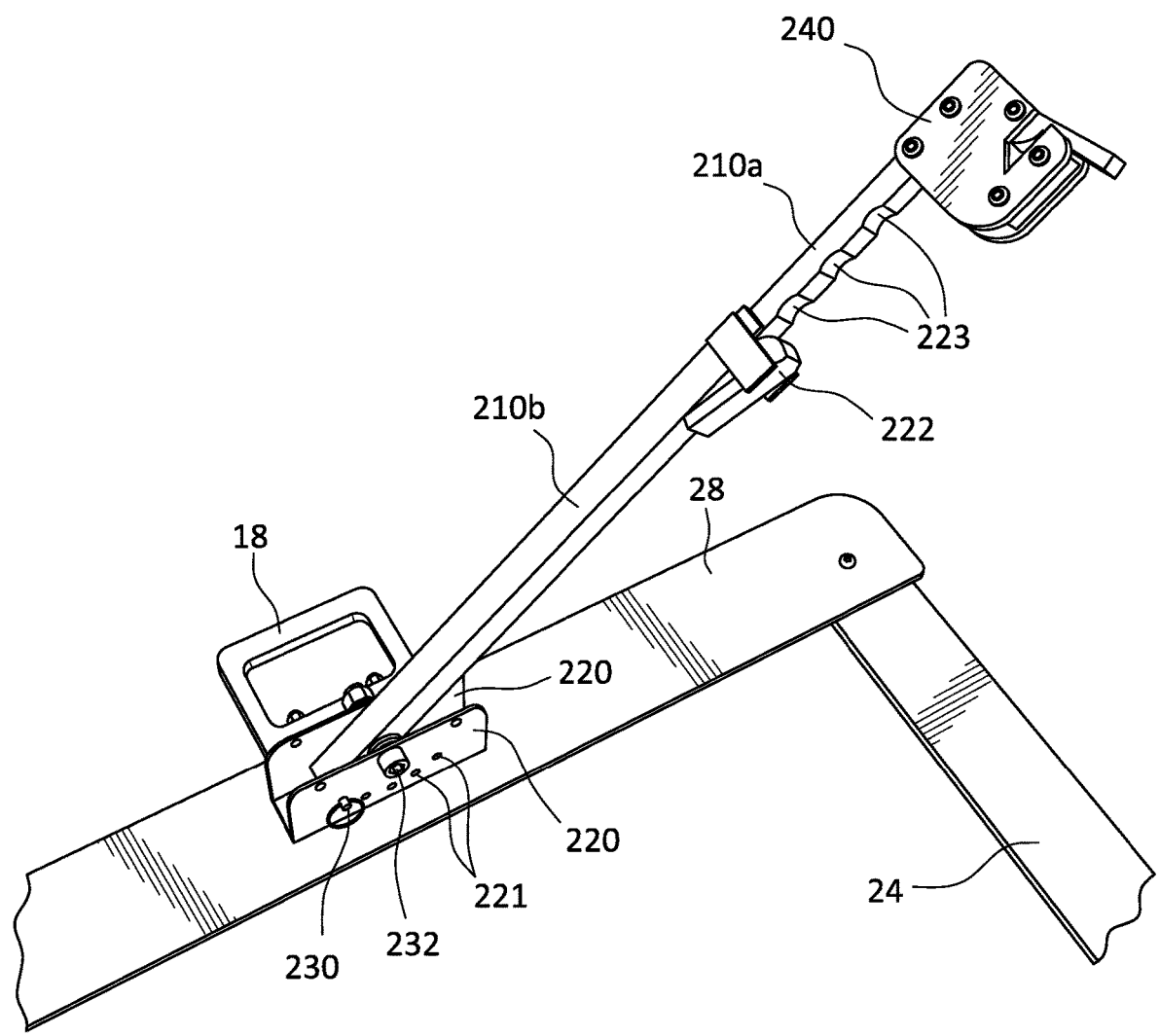
FIG. 6 is a perspective view the x-ray positioner stand of FIG. 5 with a support rod held at an oblique angle with respect to the base.

FIG. 5 is a perspective view of another embodiment of the positioner stand 200. In this embodiment, the base 12 is similar to the base 12 of the positioner stand 100 and will not be described in more detail. In the embodiment of FIG. 5, there are two pivot index plates 220 and the bottom part of the support rod 210 is received between the two pivot index plates 220. A lower part 210b of the support rod 210 is pivotably connected to the pivot index plates 220 and pivots about a pivot axis 232. Each of the pivot index plates 220 includes a plurality of holes 221 spaced circumferentially about the pivot axis 232. Each hole 221 of one of the pivot plates 220 aligns with a hole 221 in the other pivot plate 220 as a pair. A lower end of the lower part 210b of the support rod 210 receives a pin 230 that is engaged through one pair of the aligned holes 221 in the pivot index plates 220 to hold the support rod 210 in a fixed position relative to the base 12. FIG. 6 shows the support rod 210 fixed in a non-vertical position for obtaining an image at an oblique angle relative to a radiographic panel 14 (FIGS. 1 and 17 show the positioning of the radiographic panel 14).

Referring back to FIG. 5, the lower part 210b of the support rod 210 receives the upper part 210a of the support rod 210 telescopically. The upper part 210a includes indentations 223 in one of which a cam 222 is received to hold the upper part 210a in a fixed position relative to the lower part 210b. The cam 222 is pivotable from a locked position to a release position to release the upper part 210a so that a length of the support rod 210 is adjustable. In the embodiment shown in FIGS. 1 and 5, the length of the support rod 210 is adjustable in uniform increments. However, it is also possible that the spaces between the indentations 223 are not uniform and relate to different size radiographic panels used to capture the images, i.e., different lengths of the support rod at which different sized radiographic panels 14 are flooded by the x-ray generator 16. An attachment head 240 is connected at a top end of the upper part 210a of the support rod 210 for connecting to the x-ray generator 16.

Figure 7:
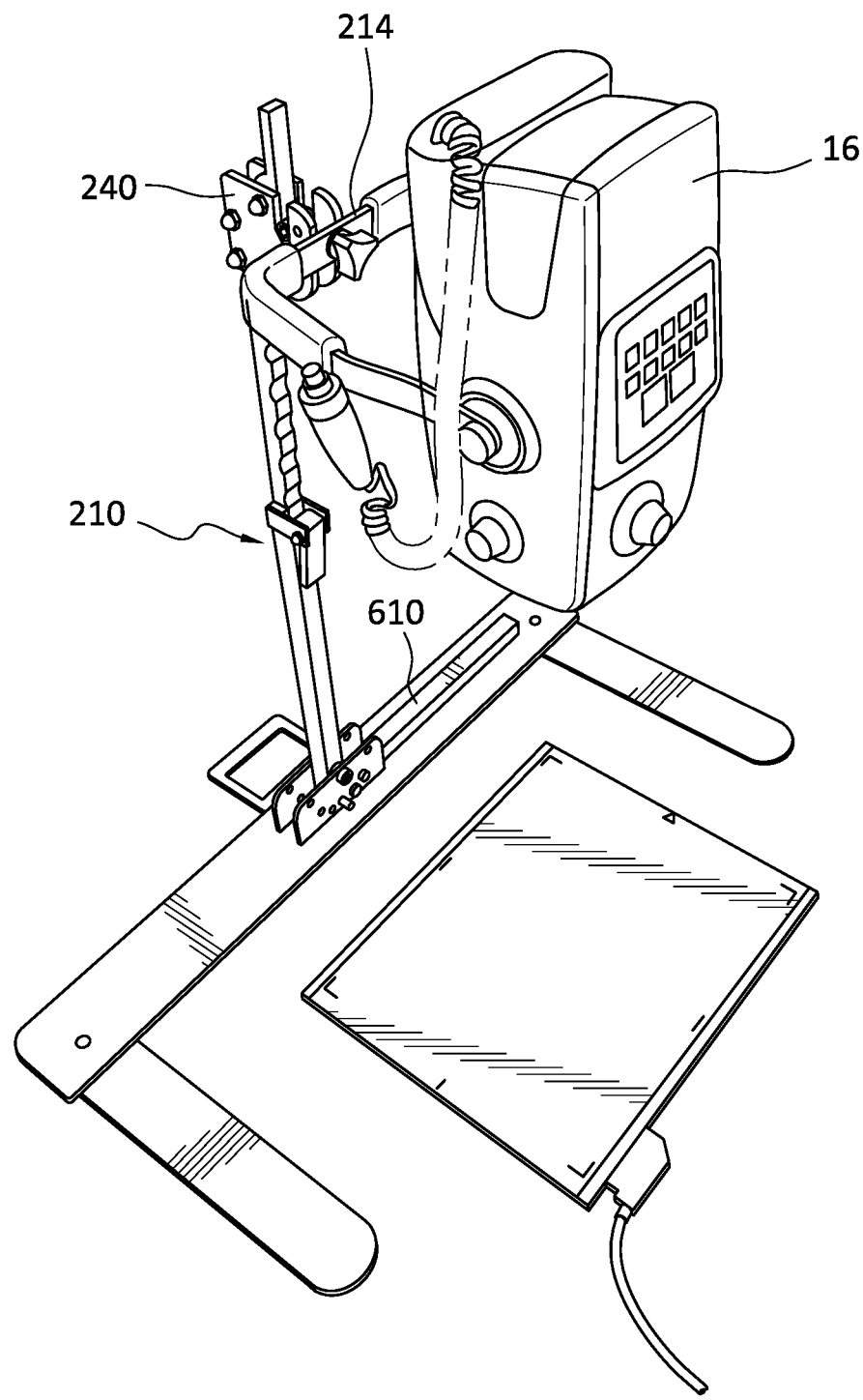
FIG. 7 is a perspective view of an x-ray positioner stand in an open position according to a further embodiment of the present invention.
Figure 8:
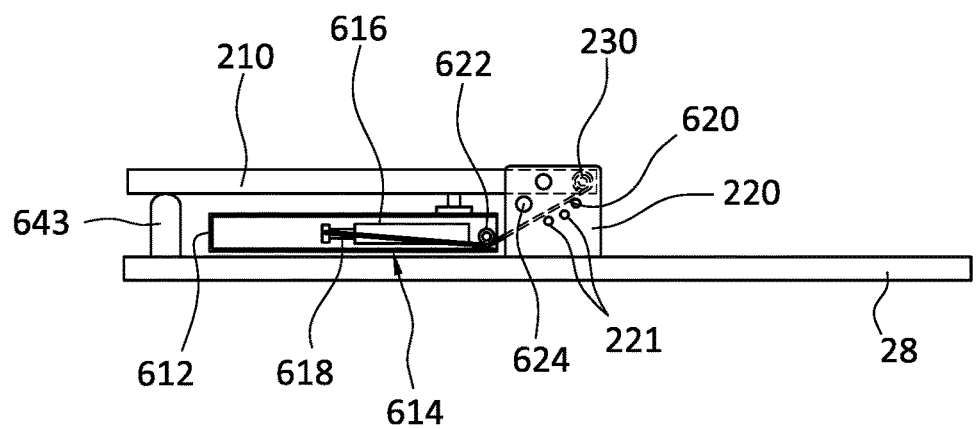
FIG. 8 is a front view of the x-ray positioner stand of FIG. 7 with the support rod in a stored position.
Figure 10:
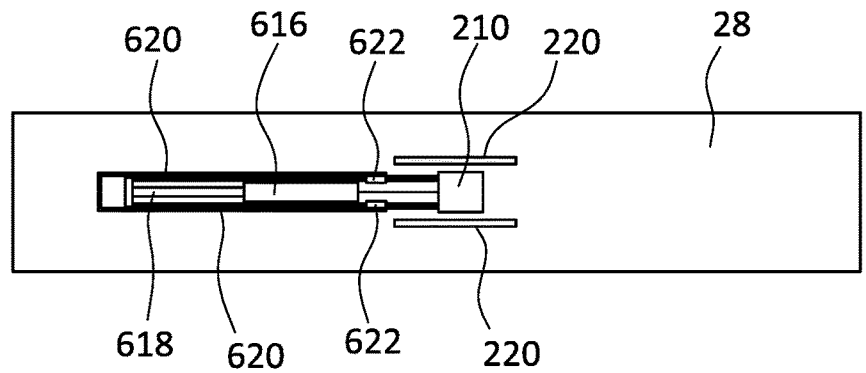
FIG. 10 is a top view of the x-ray positioner stand of FIG. 7 showing details of piston-cylinder unit.

FIGS. 7-10 show yet another embodiment of the present invention. In this embodiment, the base 12 and support rod 210 are similar to the base and support rod of FIG. 4 and will not be described in more detail. FIG. 7 shows the x-ray generator 16 connected to the attachment head 240 by a handle 214 of the x-ray generator 16. The details of the connection are described below. The embodiment of FIGS. 7-10 includes a gas spring assist mechanism 610 for raising the support rod from the travel position to the deployed position. The gas spring assist mechanism 610 has a housing 612 in which a piston-cylinder assembly 614 is arranged, the piston-cylinder assembly 614 having a cylinder 616 and a piston rod 618 extending from one end of the cylinder 616. The free end of the piston rod 618 is connected to a cable 620 that is routed around a guide 622 and connected to the lower end of the support rod 210. FIGS. 7 and 8 show the rear side of the positioner stand. As shown in FIG. 10, a second cable and guide may be arranged on the front side of the piston-cylinder assembly 614.

Figure 17:
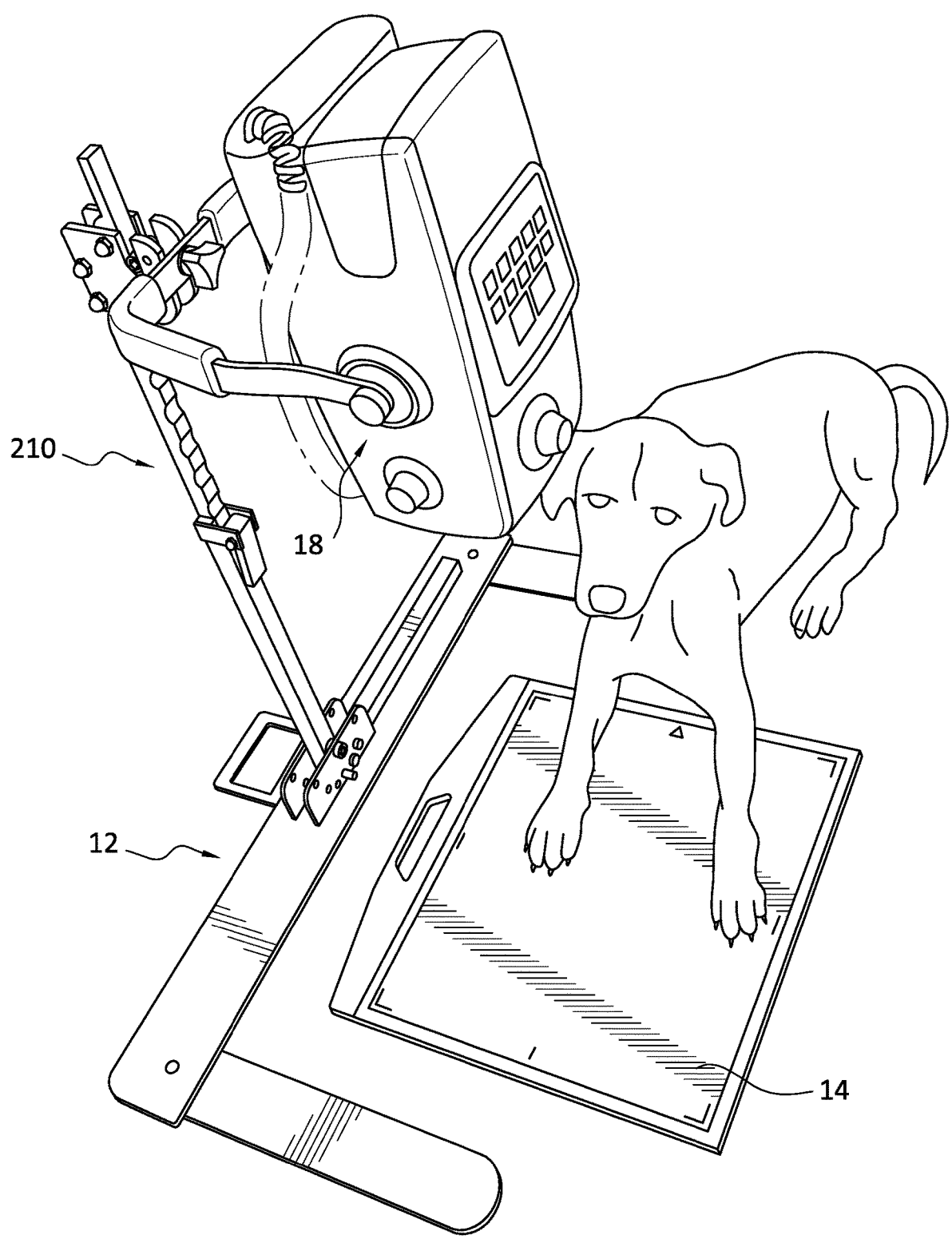
FIG. 17 is a perspective view of the embodiment of FIGS. 7-10 showing a subject to be imaged.

FIG. 17 depicts the stand in use with a part of a patient to be imaged arranged on the radiographic panel 14, which is disposed below the x-ray generator 16.

Figure 8A:
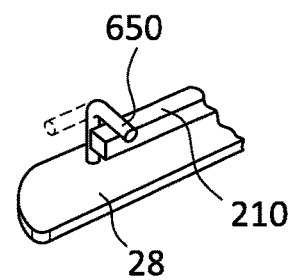
FIG. 8A is a partial view of a base of the x-ray positioner stand showing a brace for holding the support rod in the stored position.
Figure 9:
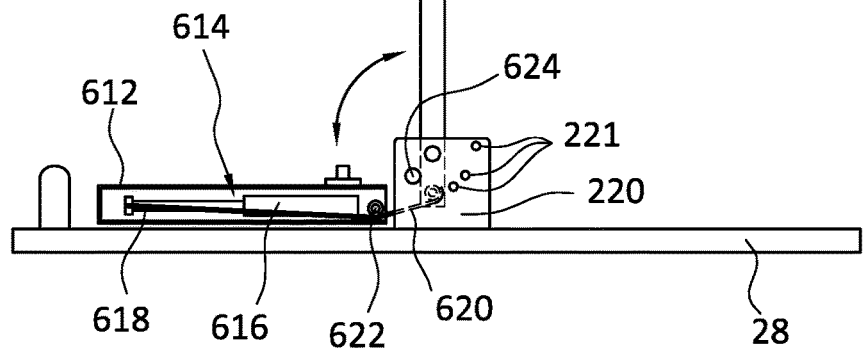
FIG. 9 is a front view of the x-ray positioner stand of FIG. 7 with the support rod in a deployed position.

During transport, the support rod is held in the transport position, e.g., by the pin 230 engaged with the pivot index plates 220 and the support rod 210. As an alternative or addition, a mechanical lock may hold the support rod 210 relative to the base plate 28. For example, a bolt 640 attached to the base plate 28 may be inserted through a hole in the support rod 210 and the support rod 210 is secured thereon by a wing nut 642 against a stopper 643 mounted on the base plate 28. FIG. 8A shows an alternative embodiment in which an L-shaped brace 650 is connected so that one leg of the brace 650 is rotatable between a locked position (shown in solid lines in FIG. 8A) and an unlocked position (shown in dashed lines in FIG. 8A).

Figure 11:
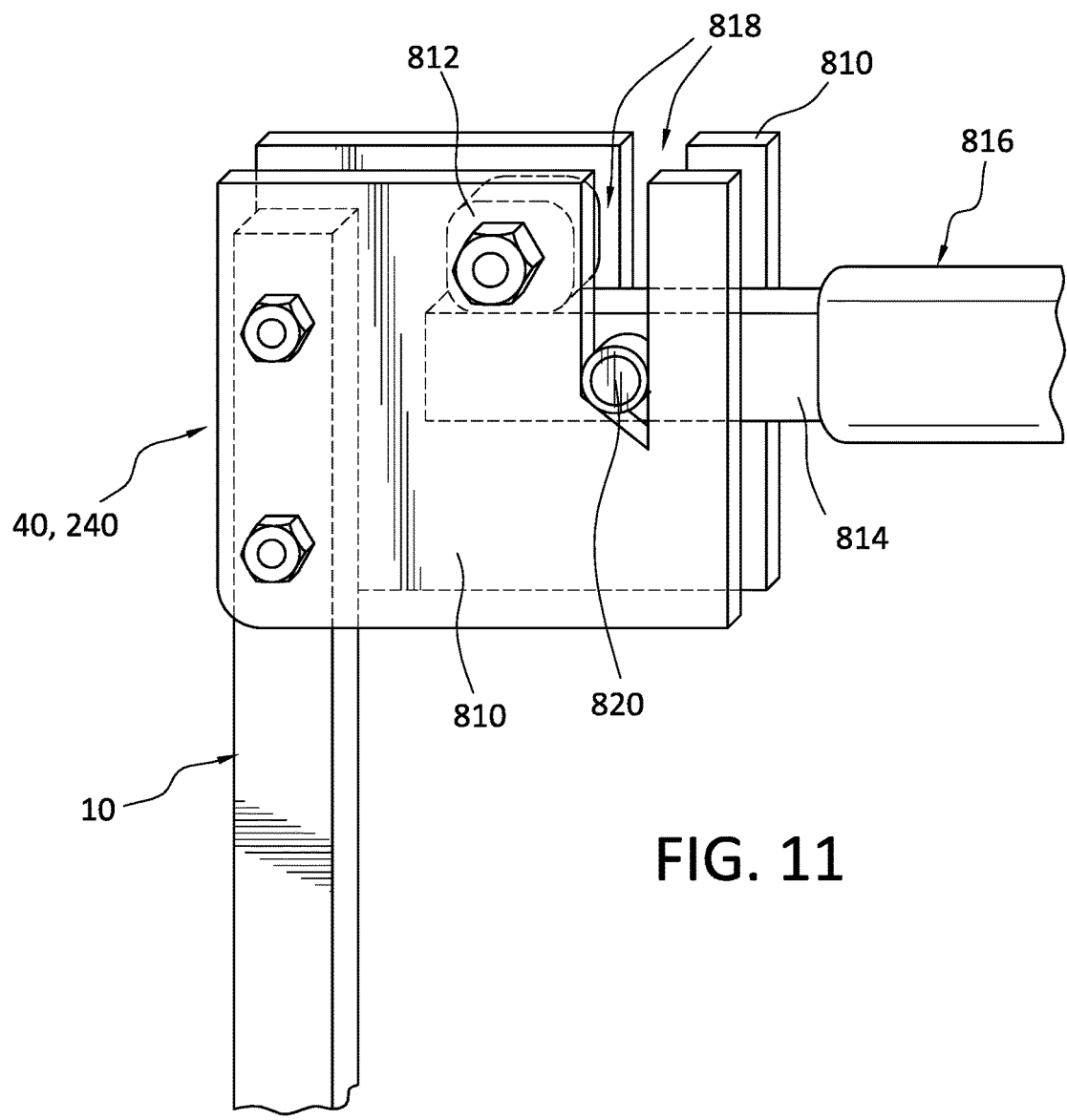
FIG. 11 is a perspective view of an embodiment of an attachment head for use with the x-ray positioner stands of the present invention.
Figures 11A, 11B:
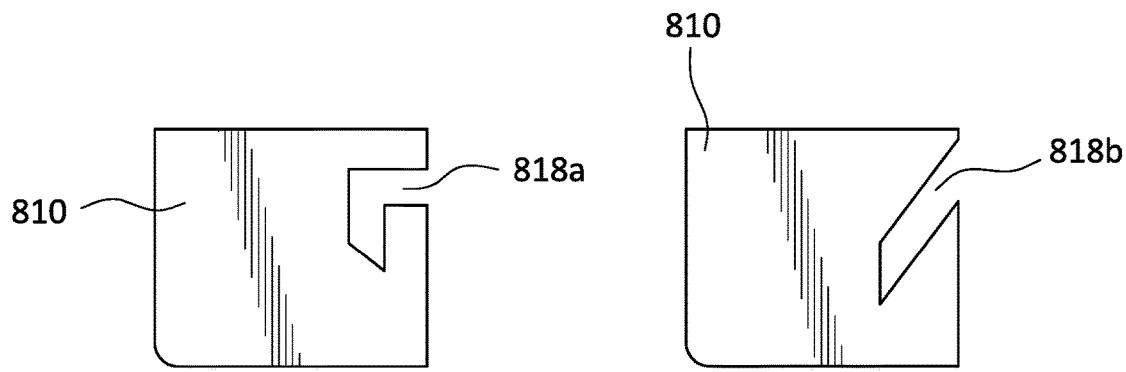
FIGS. 11A and 11B are side views of alternate embodiments of the attachment head according to the invention.
Figure 12:
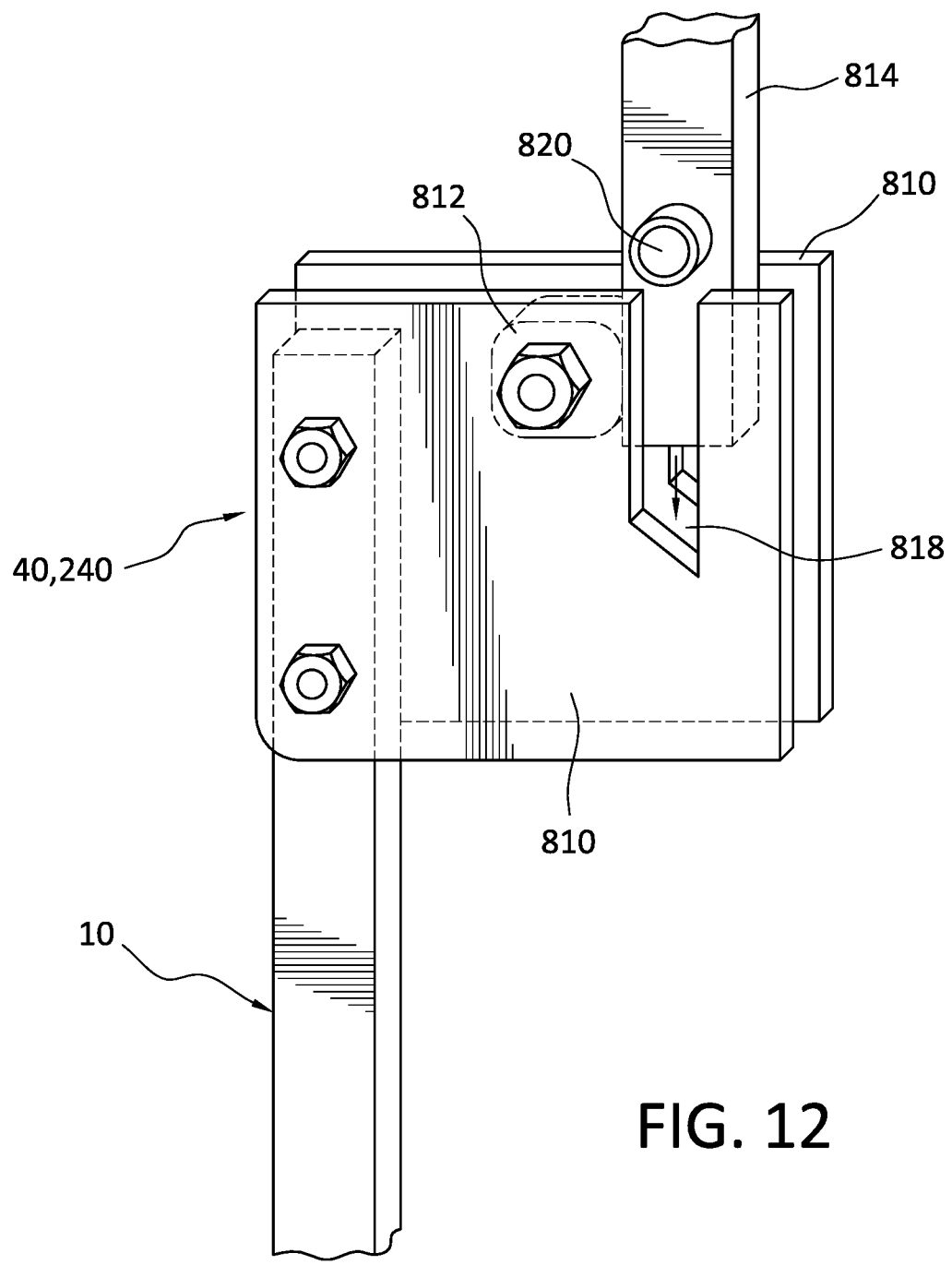
FIG. 12 is a perspective view of the attachment head of FIG. 11 showing an initial insertion step.

FIG. 11 shows an embodiment of the attachment head 40, 240 that allows a quick assembly and disassembly of the x-ray generator 16 to and from the stand. The attachment head 40, 240 includes two side plates 810, 810 connected on opposing sides of the upper part 10a of the support rod 10. The side plates are connected to the upper part by bolts. However, any know or hereafter developed connection may be used. For example, the side plates may be welded, riveted, brazed, or adhered to the upper part 10a. A bar 814 is connected to a portion of the x-ray generator 16. In the embodiments shown in FIGS. 7 and 16, the bar 814 is connected to a handle 214 of the x-ray generator 16. The bar 814 includes bosses 820 projecting from opposing sides of the bar 814 (only one is shown in FIG. 11). The bosses 820 are received in two open slots 818, 818 in the side plates 810, 810. A free end of the bar 814 between the side plates 810, 810 is held against a stop 812. The slots 818 allow the x-ray generator to be quickly inserted and removed from the attachment head 40, 240. Although the slots 818 are depicted as vertical slots, the slots 818 can have different shapes such as an L-shaped slot 818a shown in FIG. 11A and a slanted slot 818b shown in FIG. 11B.

Figure 13:
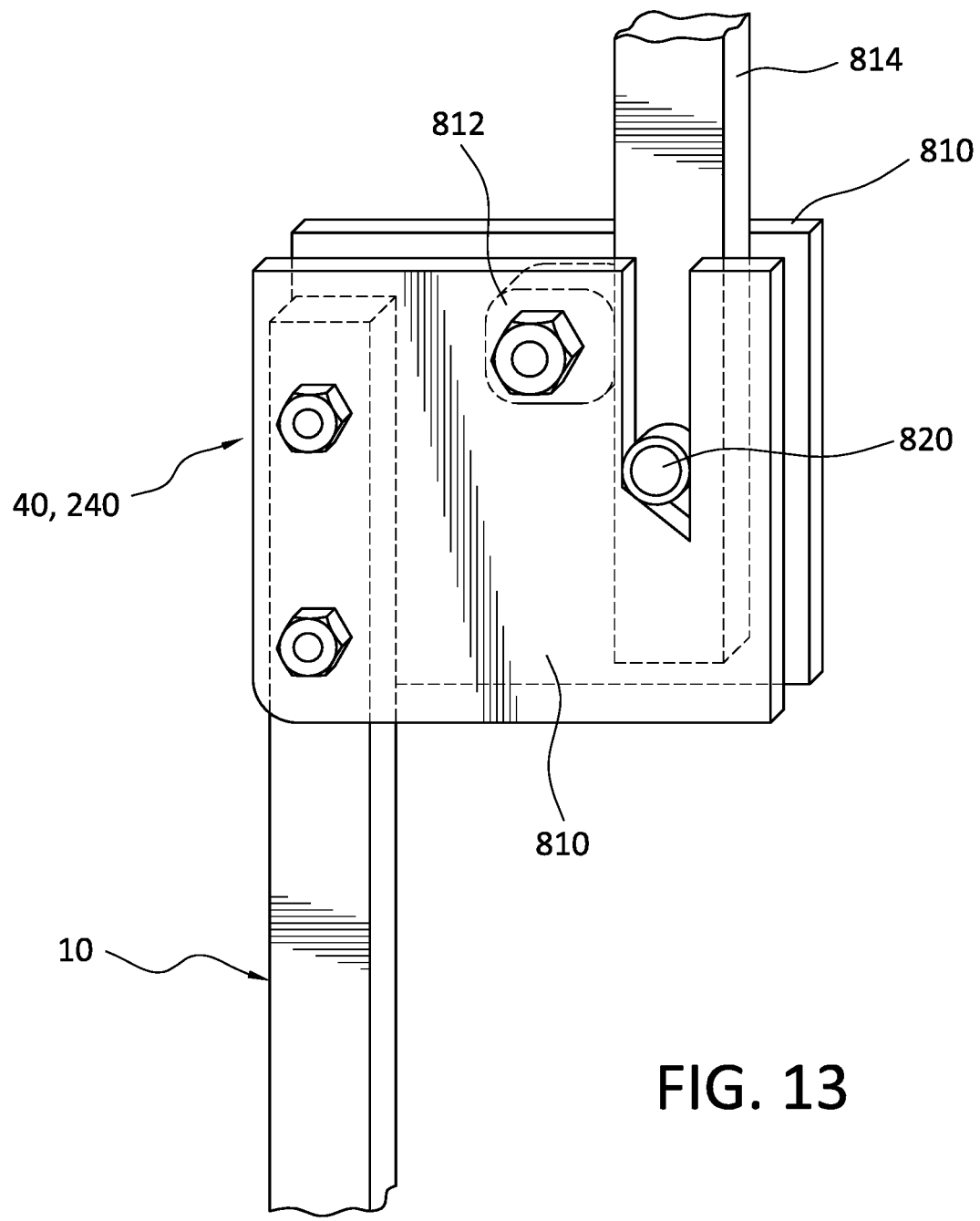
FIG. 13 is a perspective view of the attachment head of FIG. 11 after the initial insertion step is complete.
Figure 14:
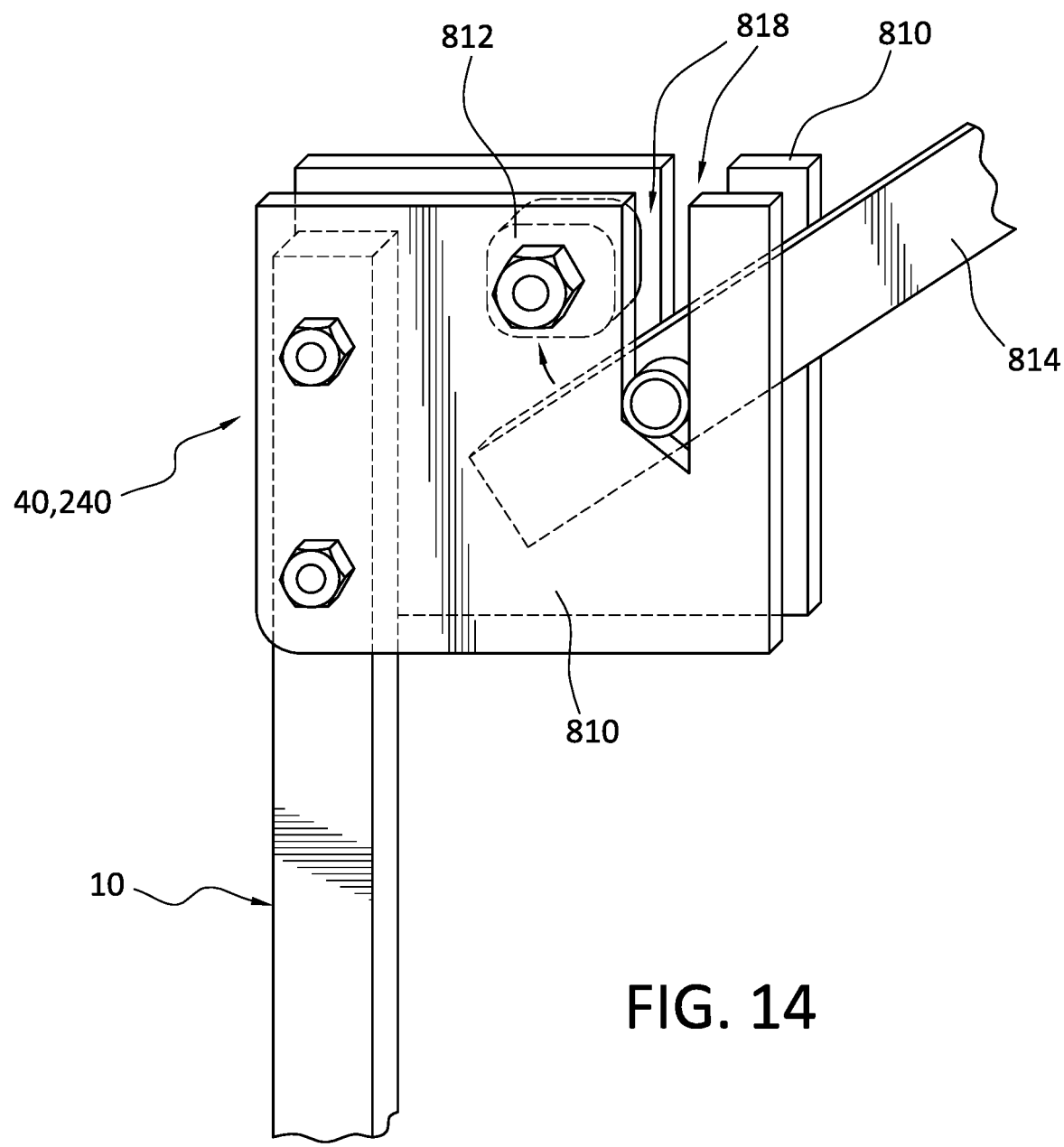
FIG. 14 is a perspective view of the attachment head of FIG. 11 during a second insertion step.
Figure 15:
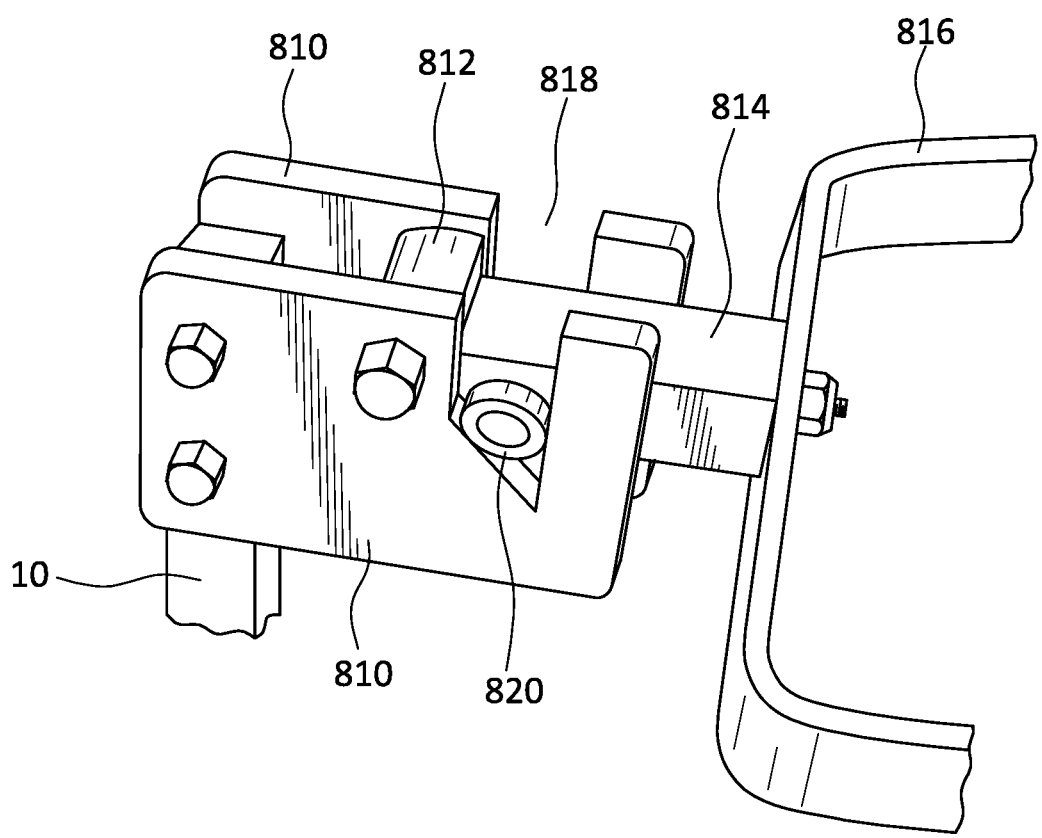
FIG. 15 is a perspective view of the attachment head of FIG. 11 after completion of the second insertion step.

FIGS. 12-15 show how the bar 814 is inserted into the attachment head 40, 240. To simplify the drawings, the handle 214 is not shown in FIGS. 12-14, but can be connected to the base 814 during these steps. Starting at FIG. 12, the bar 814 is first inserted between the side plates 810, 810 from a top of the attachment head 40, 240 during a first insertion step. The bar 814 is oriented so that a free end of the bar that is not connected to the x-ray generator 16 faces downward. The bar 814 is lowered until the bosses 820 reach the bottom of the slots 818 as shown in FIG. 13. In a second insertion step, the bar 814 is rotated about the bosses 820 until the free end of the bar 814 abuts the stop 812 as shown in FIGS. 14 and 15. FIG. 15 further shows the handle 214 of the x-ray generator 16 attached to the bar 814.

Figure 16:
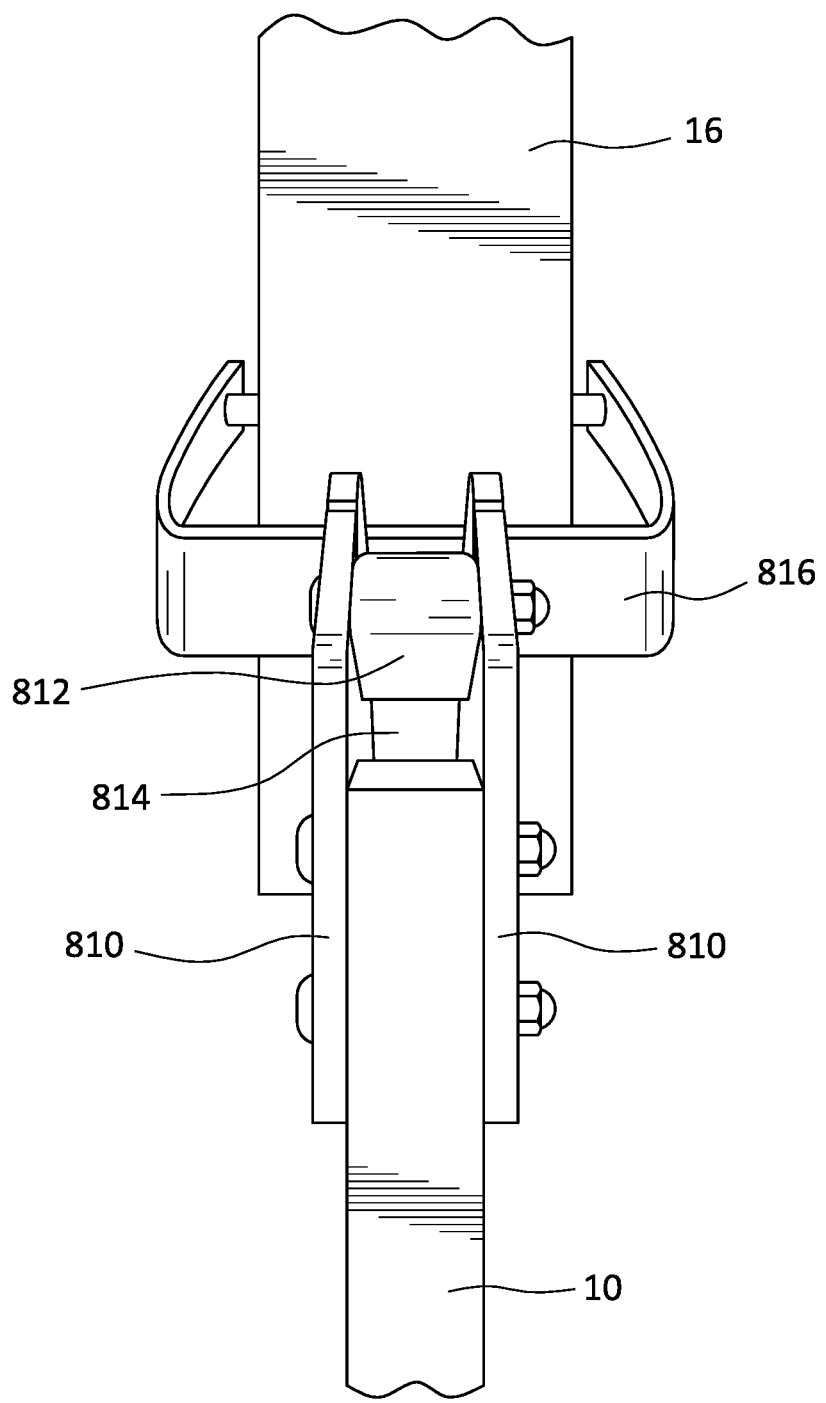
FIG. 16 is a rear view of the attachment head of FIG. 11 with the x-ray generator supported by the attachment head.

FIG. 16 shows the free end of the bar 814 abutting the stop 812 with the x-ray generator 16 connected by the handle 816 to the bar 814. To disconnect the x-ray generator 16 from the attachment head 40, 240, the steps of FIGS. 12-15 are performed in reverse.

As stated above, the attachment head 40, 240 shown in FIGS. 11-16 allows the x-ray generator 16 to be quickly attached and detached from the stand. As an alternative, a simpler connection may be used. For example, the handle 816 of the x-ray generator 16 could be connected directly to the attachment head 40, 240 by a mechanical fastener such as a bolt, or screw, of clamp. In a further embodiment, the attachment head 40, 240 could simply be the top end of the upper part 10*a*, 210*a* of the support rod 10, 210.

Thus, while there has been shown and described and pointed out the fundamental novel features of the invention is applied to a preferred embodiment thereof, it will be understood that various omissions and substitutions and changes in the form and details of the devices illustrated, and in their operation, may be made by those skilled in the art without departing from the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An x-ray positioning stand for holding an x-ray generator, comprising:
    a base including a primary base member, a first extension arm, and a second extension arm, the primary base member extending in a longitudinal direction along a length from a first end to a second end, and extending in a transverse direction along a width from a front side to a rear side, the first extension arm being pivotably connected to the primary base member proximate the first end and the second extension arm being connected to the primary base member proximate the second end; and
    a support rod having a lower end connected to a central portion of the primary base member and an upper free end having an attachment head connectable to the x-ray generator,
    each of the first extension arm and the second extension arm being pivotable from a stored position to a deployed position, wherein the base provides a support for the x-ray generator when the x-ray generator is connected to the support rod and the first extension arm and the second extension arm are in the deployed position, and wherein free ends of the first extension arm and the second extension arm are closer to each other in the stored position than in the deployed position.

2. The x-ray positioning stand according to claim 1, wherein the support rod includes an upper part and a lower part extendable with respect to each other and a locking mechanism that is movable from a locked position in which the upper part and lower part are fixed with respect to each other by the locking mechanism, and a released position in which the upper part and lower part are movable with respect to each other.

3. The x-ray positioning stand according to claim 1, wherein at least one of the first extension arm and the second extension arm includes telescopically extendable parts.

4. The x-ray positioning stand according to claim 1, wherein the support rod is pivotably connected to the base about a pivot axis, and the x-ray positioning stand further comprises a positioning device for selectively maintaining the support rod at a fixed position relative to the primary base member.

5. The x-ray positioning stand according to claim 4, wherein the positioning device includes a pivot index plate with a plurality of holes spaced circumferentially about the pivot axis and a pin that is engagable in one of the plurality of holes and the support rod to maintain the support rod at the fixed position relative to the base.

6. The x-ray positioning stand according to claim 5, wherein the support rod is pivotable to a stored position, at which the free end of the support rod is closest to the primary base member.

7. The x-ray positioning stand according to claim 1, wherein the base further includes a handle.

8. The x-ray positioning stand according to claim 7, wherein the handle is connected to the rear side of the base.

9. The x-ray positioning stand according to claim 1, wherein the primary base member is in the form of a plate having an upper surface and a lower surface, the support rod being connected at the upper surface.

10. The x-ray positioning stand according to claim 9, wherein the first extension arm and the second extension arm are connected at the lower surface of the primary base member.

11. The x-ray positioning stand according to claim 10, wherein the primary base member includes ribs on the lower surface creating pockets that receive the first extension arm and the second extension arm in the stored position.

12. The x-ray positioning stand according to claim 10, wherein the ribs include three ribs at the first end, the second end, and a central location of the primary base member, the three ribs extending in the transverse direction.

13. The x-ray positioning stand according to claim 12, wherein the ribs further include a further rib disposed along the rear side.

14. The x-ray positioning stand according to claim 1, wherein the attachment head includes two side plates separated by a space, and an x-ray generator adaptor connectable to the x-ray generator, the x-ray generator adaptor being insertable into the attachment bead between the side plates to connect the x-ray generator to the attachment head.

15. The x-ray positioning stand according to claim 14, wherein the x-ray generator adapter is a bar having a first end connectable to the x-ray generator and a second end insertable between the side plates, wherein the bar includes two bosses projecting from two opposing sides of the bar, the bosses being receivable in respective slots in the side plates.

16. The x-ray positioning stand according to claim 15, wherein each of the slots has an open end and a closed end, the closed end disposed at a bottom section of the slot.

17. The x-ray positioning stand according to claim 16, wherein the attachment head further includes a stop arranged between side plates, and
   when the bosses are received at the bottom sections of the slots and the first end of the bar is connected to the x-ray generator, the top of the second end is held against the stop by a weight of the x-ray generator at the first end.

18. The x-ray positioning stand according to claim 1, further comprising a spring connected between the base and the support rod for automatically raising the support rod from a stored position to a deployed position.

19. The x-ray positioning stand according to claim 18, wherein the spring is a gas spring comprising a piston-cylinder.

20. The x-ray positioning stand according to claim 18, wherein the spring is connected to the support rod by a cable.

* * * * *